(12) United States Patent
Harrison et al.

(10) Patent No.: US 7,863,230 B2
(45) Date of Patent: *Jan. 4, 2011

(54) LUBRICANT COMPOSITIONS, CONDOM PRODUCTS AND METHODS OF MAKING SAME

(76) Inventors: James Jeffries Harrison, 9212 Rocky Mesa Pl., West Hills, CA (US) 91304; Nohemi Harrison, 9212 Rocky Mesa Pl., West Hills, CA (US) 91304

( * ) Notice: Subject to any disclaimer, the term of this patent is extended or adjusted under 35 U.S.C. 154(b) by 970 days.

This patent is subject to a terminal disclaimer.

(21) Appl. No.: 11/389,661

(22) Filed: Mar. 24, 2006

(65) Prior Publication Data

US 2006/0240997 A1  Oct. 26, 2006

Related U.S. Application Data

(63) Continuation-in-part of application No. 11/089,953, filed on Mar. 25, 2005, now Pat. No. 7,405,186.

(51) Int. Cl.
*C10M 107/34* (2006.01)
*C07D 207/26* (2006.01)

(52) U.S. Cl. .................. 508/579; 508/268; 128/844

(58) Field of Classification Search ............... 508/268, 508/579; 128/844
See application file for complete search history.

(56) References Cited

U.S. PATENT DOCUMENTS

| | | | |
|---|---|---|---|
| 3,954,960 A | 5/1976 | Valan | |
| 4,415,548 A | 11/1983 | Reddy | |
| 4,578,203 A * | 3/1986 | Franz et al. | 508/268 |
| 4,781,847 A | 11/1988 | Weitz | |
| 5,468,401 A * | 11/1995 | Lum et al. | 508/115 |
| 5,512,289 A | 4/1996 | Tseng et al. | |
| 5,525,336 A | 6/1996 | Green et al. | |
| 5,635,169 A | 6/1997 | Blankenburg et al. | |
| 5,696,061 A | 12/1997 | Walsh | |
| 5,711,896 A | 1/1998 | Kaimai | |
| 5,747,043 A | 5/1998 | Ginoux et al. | |
| 5,785,054 A * | 7/1998 | Kelly | 128/842 |
| 5,885,591 A | 3/1999 | Ahmad et al. | |
| 5,935,636 A | 8/1999 | Nishimoto et al. | |
| 5,948,420 A | 9/1999 | Ferhut et al. | |
| 5,980,477 A | 11/1999 | Kelly | |
| 5,993,854 A | 11/1999 | Needleman et al. | |
| 6,054,422 A | 4/2000 | Ward et al. | |
| 6,123,933 A | 9/2000 | Hayama et al. | |
| 6,139,848 A | 10/2000 | Ahmad et al. | |
| 6,180,124 B1 | 1/2001 | Ohta et al. | |
| 6,196,227 B1 | 3/2001 | Tsushima | |
| 6,287,580 B1 | 9/2001 | Gott et al. | |
| 6,440,429 B1 | 8/2002 | Torizuka et al. | |
| 6,495,150 B2 | 12/2002 | Bekele | |
| 6,534,090 B2 | 3/2003 | Puthli et al. | |
| 6,548,456 B1 * | 4/2003 | Mulder et al. | 508/268 |

(Continued)

*Primary Examiner*—Glenn A Caldarola
*Assistant Examiner*—Vishal Vasisth
(74) *Attorney, Agent, or Firm*—Stout, Uxa, Buyan & Mullins; Carlos A. Fisher

(57) ABSTRACT

Warming personal lubricant compositions, condom products including such compositions and methods of making such condom products are disclosed. The present warming lubricant compositions include at least about 50% by weight of a polyalkylene glycol component, preferably including at least two portions of different molecular weights, and an effective amount of a viscosity inducing component.

9 Claims, 1 Drawing Sheet

U.S. PATENT DOCUMENTS

| | | |
|---|---|---|
| 6,630,163 B1 | 10/2003 | Murad |
| 6,663,855 B2 | 12/2003 | Frechet et al. |
| 6,673,374 B2 | 1/2004 | Murad |
| 6,685,925 B2 | 2/2004 | Hajduk et al. |
| 6,709,648 B2 | 3/2004 | Sako et al. |
| 6,752,998 B2 | 6/2004 | Verdrel-Lahaxe et al. |
| 7,005,408 B2 * | 2/2006 | Ahmad et al. ............... 508/219 |
| 7,086,403 B2 | 8/2006 | Harrison et al. |
| 2003/0059489 A1 * | 3/2003 | Letourneau et al. ......... 424/776 |
| 2003/0207772 A1 | 11/2003 | Ahmad et al. |
| 2003/0211161 A1 | 11/2003 | Ahmad et al. |
| 2003/0232090 A1 | 12/2003 | Ahmad et al. |
| 2004/0037911 A1 * | 2/2004 | Letourneau et al. ......... 424/776 |
| 2004/0138074 A1 | 7/2004 | Ahmad et al. |
| 2004/0167039 A1 | 8/2004 | Ahmad et al. |
| 2004/0185065 A1 | 9/2004 | Ahmad et al. |
| 2005/0241982 A1 | 11/2005 | Muni et al. |

* cited by examiner

LUBRICANT COMPOSITIONS, CONDOM PRODUCTS AND METHODS OF MAKING SAME

RELATED APPLICATION

This application is a continuation-in-part of U.S. patent application Ser. No. 11/089,953, now U.S. Pat. No. 7,405,186, filed Mar. 25, 2005, the disclosure of which is hereby incorporated in its entirety by reference.

BACKGROUND OF THE INVENTION

The present invention relates to lubricant compositions, condom products including lubricant compositions and methods of making condom products. More particularly, the invention relates to warming lubricant compositions, for example, personal lubricant compositions, condom products including condoms lubricated with warming lubricant compositions, and method of making such condom products.

Personal lubricants, for example, in the form of pourable liquids, pourable low viscosity thixotropic gels, jellies and the like, are known and are useful for providing lubricity to various parts of the human body, for example, to mucous membranes, such as the oral, rectal, vaginal and the like mucosa. For example, see Ahmad et al U.S. Pat. No. 5,885,591, the disclosure of which is incorporated in its entirety herein by reference. Certain such lubricants have been proposed which generate heat or warming when placed in contact with the human body.

Using condoms lubricated with warming lubricants has also been proposed. Producing such lubricated condoms is somewhat challenging, particularly if the lubricant is to be applied both inside and on the outside of the condom. Conventional machinery used in condom manufacture mandates that the lubricant composition has relatively tight specifications, for example, in terms of viscosity, tackiness and stringiness, as well as providing the desired degree of lubricity and warming or heat generation.

There continues to be a need for new warming lubricant compositions, condom products including warming lubricants and methods of making such condom products.

SUMMARY OF THE INVENTION

New lubricant compositions, condom products and methods of making condom products have been discovered. The present lubricant compositions have chemical make-ups which provide for enhanced/increased heat generation or warming, for example, relative to one or more prior art lubricants. In addition, the present compositions can have relatively widely varying chemical make-ups, and therefore, can be employed in many applications, for example, as stand alone lubricant products, for example, personal lubricant products, in combination with one or more medications, such as anti-fungal agents and the like, and/or in combination with devices, such as condoms and the like. In one embodiment, the present lubricant compositions are particularly useful to provide lubrication for condoms, for example, in packaged condom products.

In general, the present lubricant compositions are relatively straightforward in make-up and manufacture. The compositional flexibility of the present lubricants is one important aspect in providing useful methods of making condom products. Such compositions are effective and enjoyable in use, whether as a stand-alone product or in combination with one or more medications and/or devices.

In one broad aspect, the present lubricant compositions comprise a polyalkylene glycol component present in an amount of at least about 50% by weight of the composition; and an effective amount of a viscosity inducing component, preferably other than a cellulosic derivative. The compositions are substantially clear or transparent and substantially anhydrous, and are effective to generate heat or warming when placed in contact with water, for example, when placed in contact with a living human, such as a mucous membrane of a living human. In one useful embodiment, the present compositions may be in the form of massage lubricants which are very effective when used on moist parts of the body (the human body) including mucus membrane tissue and/or non-mucus membrane tissue.

The viscosities of the present compositions can be varied over a relatively broad range depending, for example, on the particular application for which the composition is to be used. For example, the present compositions can have a viscosity, at 25° C., in a range of about 50 cps or less to about 5000 cps or about 10,000 cps or more. In situations where the lubricant composition is designed for use as a stand alone personal lubricant or as a lubricant for a condom, for example, a packaged lubricated condom product, viscosities (at 25° C.) of less than about 500 cps or less than about 750 cps or less than about 1000 cps or less than about 2000 cps, for example, in a range of about 50 cps or about 100 cps or about 300 cps to less than about 500 cps or less than about 750 cps or less than about 1000 cps or less than about 2000 cps are advantageously useful.

In one very useful embodiment, the polyalkylene glycol component, preferably a polyethylene glycol component, comprises a first polyalkylene glycol component portion having a first molecular weight and a second polyalkylene glycol component portion having a second molecular weight which is reduced relative to the first molecular weight. In one embodiment, the second molecular weight is less than about 270. A composition including both the first and second polyalkylene glycol component portions has a somewhat reduced warming or heat generating effect relative to a substantially identical composition without the second polyalkylene glycol component. However, a composition including both first and second polyalkylene glycol portions, preferably first and second polyethylene glycol portions, advantageously has a reduced cloud point temperature and/or a reduced solidification point or temperature relative to a substantially identical composition without the second polyalkylene glycol portion. Preferably, the present lubricant compositions are substantially clear or substantially transparent at temperatures in a range of about 20° C. to about 30° C., for example, 25° C.

The weight ratio of the first polyalkylene glycol component portion to the second polyalkylene glycol portion may vary over a relatively wide range, for example, from about 0.1 to about 10. Such ratio may be less than about 7 or less than about 3 or less than about 1.3 or lower.

In one very useful embodiment, the second polyalkylene glycol component portion is present in a greater amount by weight than the first polyalkylene glycol component portion. For example, the second polyalkylene glycol component portion may be present in the composition in an amount in a range of about 1.1 or about 1.5 or about 2 to about 4 or about 5 or more times the amount of the first polyalkylene glycol component portion in the composition. Using an excess of the second polyalkylene glycol component portion facilitates maintaining the composition substantially clear or transparent, for example, during transportation or periods of storage or at varying temperatures, such as temperatures below room or ambient temperature, e.g., temperatures below about 22° C.

The polyalkylene glycol component, for example, the first and second polyalkylene glycol component portions combined or together, may be at least about 70% by weight or at least about 80% by weight or at least about 90% by weight of the composition. The present compositions preferably have an enhanced ability to generate heat when placed in contact with water or when placed in contact with a mucous membrane of a living human, relative to a similar or substantially identical composition containing a reduced amount, for example, at least 5% by weight less, of the polyalkylene glycol component.

The polyalkylene glycol components, and component portions, may have molecular weights varying over relatively wide ranges, for example, in a range of about 100 or about 150 to about 1000 or about 3000 or about 5000 or more. In one embodiment, first polyalkylene, for example, polyethylene, glycol component portion preferably has a molecular weight in a range of about 350 to about 450. The second polyalkylene, for example, polyethylene, glycol component portion preferably has a molecular weight in a range of about 150 to about 250.

The viscosity inducing components of the present lubricant compositions may be selected from any materials or combination of materials effective to increase the viscosity, and advantageously the lubricity, of the lubricant compositions, and which are compatible, that is, are substantially non-interfering, with or in the other components of the compositions and with or in the application in which the compositions are used. In one very useful embodiment, the viscosity inducing component comprises a polyvinylpyrrolidone component. Such polyvinylpyrrolidone components are effective in the present lubricant compositions to increase viscosity, and to provide enhanced lubrication when in contact with moisture relative to a composition, for example, a substantially identical composition without the polyvinylpyrrolidone component. Advantageously, the polyvinylpyrrolidone component comprises a first polyvinylpyrrolidone component portion and a second polyvinylpyrrolidone component portion having a different molecular weight than the first portion. The polyvinylpyrrolidone component may further include a third polyvinylpyrrolidone component portion having a different, for example, reduced or lower, molecular weight relative to the molecular weights of both the first and second polyvinylpyrrolidone component portions.

In a particularly useful embodiment, the relative amounts of the first and second polyvinylpyrrolidone component portions, and the third polyvinylpyrrolidone component portion, if present, are selected to provide the desired viscosity and to be effective in controlling at least one, and preferably both, of the tackiness of the lubricant composition and the stringiness of the lubricant composition. For example, a composition including a high molecular weight polyvinylpyrrolidone component and no lower molecular weight polyvinylpyrrolidone component achieves a higher viscosity, but also may have an undesirable degree of tackiness and/or stringiness. The tackiness and/or stringiness of the lubricant composition is of substantial importance, for example, when the composition is employed to lubricate a condom, for example, during the making of a lubricated condom product.

Compositions in accordance with the present invention which include a polyvinylpyrrolidone component portion having an average molecular weight which is different and reduced or lower, for example, in a range of about 5000 to about 15,000, relative to the molecular weight or weights of the other polyvinylpyrrolidone portion or portions present have increased viscosity relative to the composition without the lower molecular weight portion and advantageously do not have the increased stringiness of a substantially similar or identical composition having the same increased viscosity as the composition (which includes the lower molecular weight polyvinylpyrrolidone component portion) without the lower molecular weight polyvinylpyrrolidone component portion. In other words, a lubricant composition in accordance with the present invention including one or more higher molecular weight polyvinylpyrrolidone component portions and a lower molecular weight polyvinylpyrrolidone component portion has increased viscosity because of the presence of the lower molecular weight portion, but does not have the increased stringiness apparent in a similar composition including no lower molecular weight polyvinylpyrrolidone component portion and having its viscosity increased by an increased amount of the one or more higher molecular weight polyvinylpyrrolidone component portions.

Lubricant compositions including such reduced or lower molecular weight polyvinylpyrrolidone component portions have been found to adhere better to condoms and/or provide better or enhance feel or texture to users of condoms lubricated with the compositions or to users of the compositions as stand alone products relative to substantially identical compositions having the same viscosities without the reduced molecular weight polyvinylpyrrolidone component portions.

In another broad aspect of the present invention packaged condom products are provided. Such products comprise: a condom, for example, comprising latex, one or more other naturally occurring materials, such as animal intestine material and the like, one or more other synthetic materials, such as synthetic polymeric materials and the like, and mixtures thereof; a lubricant composition, as described elsewhere herein; and a package containing the condom and the lubricant composition. The package, containing the condom and the lubricant composition, is sealed for transportation and storage prior to use. In one embodiment, the condom includes an inner wall and an opposing outer wall both of which are in contact with the lubricant composition. The package may be made of any suitable material or combination of materials. In one embodiment, the package comprises at least one of metal foil and polymeric packaging material.

In a further broad aspect of the invention, methods of making or manufacturing condom products are provided. Such methods comprise: providing a condom; contacting the condom with a lubricant composition, as described elsewhere herein, in an amount effective to lubricate the condom for use; placing the lubricated condom in a package; and, thereafter, sealing the package, thereby forming a sealed package in which the condom and lubricant composition are substantially anhydrous.

Each and every feature described herein, and each and every combination of two or more of such features, is included within the scope of the present invention provided that the features included in such a combination are not mutually inconsistent.

These and other aspects and advantages of the present invention will become apparent when considered in light of the following detailed description, claims and drawing in which like parts bear like reference numerals.

DETAILED DESCRIPTION

Figure 1:
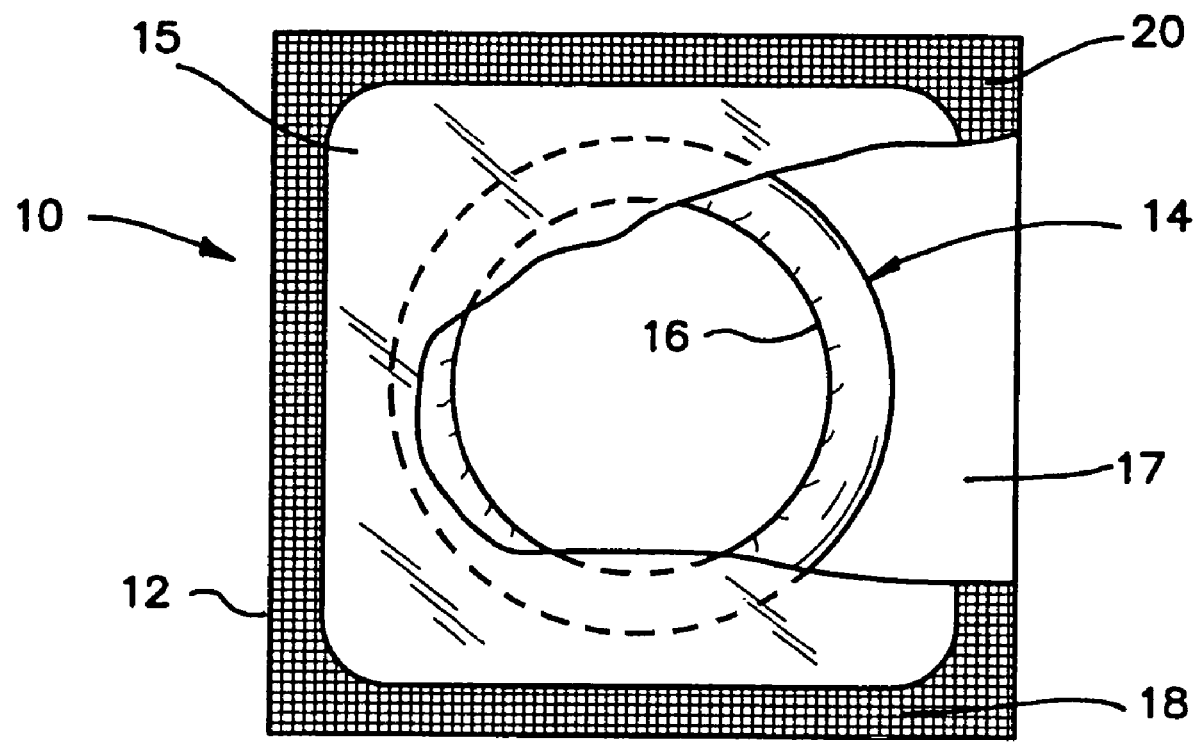
FIG. 1 is a front view, partly in cross-section of a sealed package containing a lubricated condom in accordance with the present invention.

The lubricant compositions of the present invention are substantially anhydrous, preferably containing less than about 10% by weight of water, more preferably less than about 5% by weight of water and still more preferably containing less than about 3% by weight of water. In one very useful embodiment, the present compositions are substantially free of water. In general, all other things being equal, the smaller the amount of water present in the composition the greater the heat generating ability of the composition.

The present lubricant compositions comprise a polyalkylene glycol component and a viscosity inducing component. The polyalkylene glycol components may include polyalkylene glycols, polyalkylene glycol ethers, for example, polyalkylene glycol stearates, oleates, cocoates, and the like and mixtures thereof. Although, any suitable polyalkylene glycol component may be employed, advantageously, the polyalkylene glycol component is selected from polyethylene glycols (hereinafter referred to as PEG's), polyethylene glycol ethers, and the like and mixtures thereof. PEGylated compounds, such as peptide or protein derivatives obtained by PEGylation reactions may also be used. In addition, block copolymers of PEG's may be used, such as (ethyleneglycol)-block-poly (propyleneglycol)-block(polyethylene glycol), poly(ethylene glycol-propylene glycol) (ramdon copolymer) and the like and mixtures thereof. The compositions of this invention comprise at least about 50% by weight of the polyalkylene glycol component, more preferably at least about 70%, about 80% or about 90% by weight of the composition.

In one very useful embodiment, the polyalkylene glycol component is present in different portions having different molecular weights. For example, in one embodiment the lubricant compositions of the present invention comprise a first polyalkylene glycol component portion having a first molecular weight and a second polyalkylene glycol component portion having a second molecular weight reduced relative to the first molecular weight. It has been found that controlling the molecular weight of the polyalkylene glycol component and maintaining a relatively high concentration of the polyalkylene glycol component are effective in providing the present lubricant compositions with a substantially advantageous combination of benefits. For example, the present compositions provide an increased or enhanced degree of warming, for example, relative to similar compositions which have less than about 50% by weight or less than about 30% by weight of the polyalkylene glycol component. In addition, the lubricant compositions are substantially clear, and a relatively wide range of desired viscosities can be easily obtained without substantial interference with other important properties, for example, tackiness and stringiness, of the present lubricant compositions. In short, in certain embodiments of the present invention it is highly advantageous to have two polyalkylene glycol component portions of differing molecular weights, the relative proportions of which are advantageously controlled to provide substantial benefits to the present compositions.

Polyalkylene glycol components, for example polyethylene glycol components, and component portions, may have molecular weights varying over relatively wide ranges, for example in a range of about 100 or about 150 to about 1000 to about 3000 or about 5000 or more. In one very useful embodiment, the first polyalkylene, for example, polyethylene glycol component portion preferably has a molecular weight in the range of about 350 to about 450. The second polyalkylene, for example, polyethylene glycol component portion preferably has a molecular weight of less than about 270, and more preferably in a range of about 150 to about 250. When two polyalkylene glycol component portions are used together the molecular weight difference between the two portions is preferably at least about 100 or about 150 to about 300 or about 500 or about 1000 or more.

In one very useful embodiment, the first polyethylene glycol component preferably has a molecular weight of about 350 to about 450, and is identified as PEG 400; and the second polyethylene glycol component portion has a molecular weight in a range of about 150 to about 250, and is preferably identified as PEG 200.

One important advantage of the present compositions is that the lubricant compositions of the present invention have a reduced cloud point temperature relative to a similar or substantially similar composition without the second polyalkylene glycol component portion. For example, by including a second polyalkylene glycol component portion comprising PEG 200, a composition which also includes PEG 400 has a reduced cloud point temperature relative to a similar composition which includes no PEG 200, for example, which includes an amount of PEG 400 equal to the total amount of PEG 400 and PEG 200 present in the composition. Providing a lubricant composition with a reduced cloud point temperature advantageously enhances the ability of the composition to remain clear or substantially clear over a broader range of temperatures.

The weight ratio of the first polyalkylene glycol component portion to the second polyalkylene glycol portion may vary over a relatively wide range, for example, from about 0.1 to about 10. Such ratio may be less than about 7 or less than about 3 or less than about 1.3 or lower, for example, less than about 1.0 or less than about 0.5 or lower.

In one very useful embodiment, the lower molecular weight second polyalkylene glycol component portion is present in a greater amount by weight than the higher molecular weight first polyalkylene glycol component portion. For example, the second polyalkylene glycol component portion such as a polyethylene glycol component portion having a relatively low molecular weight, may be present in the composition in an amount in a range of about 1.1 or about 1.5 or about 2 to about 4 or about 5 or more times the amount of the first polyalkylene glycol component portion, such as a polyethylene glycol component portion having a relatively high molecular weight, in the composition. Using an excess of the second polyalkylene glycol component portion facilitates maintaining the composition substantially clear or transparent, for example, during transportation or periods of storage or at varying temperatures, such as temperatures below room or ambient temperature, e.g., temperatures below about 22° C.

The present compositions include an effective amount of a viscosity inducing component. As noted elsewhere herein, the viscosity inducing component may be selected from any material or combination of materials effective to increase, preferably controllably increase, the viscosity of the composition. The presently useful viscosity inducing components advantageously are compatible, that is are substantially non-interfering with or in the other components of the composition and with or in the application in which the composition is used. In one embodiment, the viscosity inducing component is other than a cellulosic derivative, although in other of the present lubricant compositions cellulosic derivatives may be employed. In one embodiment, the present compositions are substantially free of any cellulosic derivatives.

In a very useful embodiment of the present invention, the viscosity inducing component comprises a polyvinylpyrrolidone component. Such polyvinylpyyrolidone (PVP) component is very effective in providing controlled increases in viscosity at relatively low concentrations while, at the same time, providing increases in lubricity to the present compositions.

Advantageously, the PVP component comprises a first PVP component portion and a second PVP component portion having a different molecular weight than the first portion. The PVP component may include a third PVP component portion having a different, and preferably reduced, molecular weight then both the first and second PVP component portions. The relative amounts of the first and second, and third if present, PVP component portions may be selected to be effective in controlling at least one, and preferably both, of the tackiness of the composition and the stringiness of the composition. The tackiness and/or stringiness of the present compositions are of substantial importance, for example, when the composition is employed to lubricate a condom, for example during the making of such a lubricated condom product. In addition, even as a stand-alone lubricant product, for example, for use as a personal lubricant, the present lubricant compositions advantageously have controlled tackiness and/or controlled stringiness to be an esthetically pleasing product, for example, being substantially uniform and/or smooth and/or having a substantially consistent texture, when applied to the human body. Preferably, the compositions of the present invention contain about 1% to about 15%, more preferably about 2% to about 10% by weight of the viscosity inducing component, for example the PVP component.

In the event that a first viscosity inducing component portion and a second viscosity inducing component portion having a reduced molecular weight relative to the first portion are employed in the present lubricant compositions, the relative amounts of the first and second portions may vary over a relatively wide range, for example, to facilitate providing a composition having the desired properties for any one of a number of relatively widely varying applications. For example, the weight ratio of first portion to second portion may range from about 0.05 or about 0.1 to about 0.3 or about 0.5 or about 1 or higher. In the event first and second PVP portions are employed, the weight ratio of first portion to second portion is advantageously in the range of about 0.1 to about 0.3.

The molecular weight of the viscosity inducing component may be in a range of about 5000 or about 10,000 to about 100,000 or about 1,500,000 or higher.

In one embodiment, the present compositions include a first PVP component portion having a molecular weight in a range of about 100,000 to about 1,500,000 or higher, for example, about 300,000 to about 1,000,000; and a second PVP component portion having an average molecular weight in a range of about 25,000 to about 90,000, for example, about 35,000 to about 55,000. A reduced or lower molecular weight, for example, a third, PVP component portion may be present, as discussed elsewhere herein, and advantageously have an average molecular weight of about 3000 to about 20,000, for example, about 5,000 to about 15,000.

The present lubricant compositions increase in temperature upon exposure to moisture from the skin or mucosa, without causing undue irritation or harm to the skin or mucosal surfaces.

This warming occurs by the exothermic release of energy generated upon exposing the compositions to water. The temperature increase advantageously falls within a comfort range from the minimum perceptible temperature increase to no more than that perceived as too hot, for example, causing irritation or other harm to the skin or mucosa.

Without wishing to limit the invention to any particular theory of operation, it is believed that the polyalkylene glycol components in the present compositions are useful as warming or heat-generating agents. The viscosity inducing component is useful to increase, preferably controllably increase the viscosity of the lubricant. The present compositions are advantageous in that they lubricate, warm, and soothe the tissues of the user, especially the oral and vaginal mucous membranes. Moreover, they are advantageously smooth and lubricating, rather than being stringy and tacky.

The present compositions may be in the form of a liquid, a semi-solid, or a solid depending upon the particular intended use thereof. The present compositions may be formulated as syrupy liquid-gels pourable gels or thick jellies or as pourable liquids. Preferably, the viscosities are in a range of about 50 cps or about 100 cps to less than about 500 cps or less than about 1000 cps or less than about 2000 cps. However, as noted above, viscosities in the present compositions may range from about 1000 cps to about 10,000 cps for gel, and from 60,000 cps to about 500,000 cps or more for the jellies. The present compositions may also be formulated into soft or hard gelatin capsules, suppositories and impregnated into fabrics or polymers.

A preservative component may be added to guard against microbial growth. The preservative component may be selected from preservatives known to those of skill in the art, including, but not limited to, one or more of the following: methylparaben, benzoic acid, sorbic acid, gallic acid, propylparaben and the like and mixtures thereof. The preservative component may be present, if at all, in the present compositions in an amount in a range of about 0.01% or less to about 0.5% or more by weight.

The compositions of this invention may be used as personal lubricants which convey a feeling of warmth. The feeling of warmth generated by the compositions of this invention is soothing to the skin or mucous membranes where they are applied. The compositions of the invention may also possess a sweet and pleasant taste, and may optionally include effective amounts of sweetening agents and/or flavoring agents which are of particular benefit when these compositions are used orally.

The compositions of this invention may also be used as personal moisturizers, which convey a feeling of warmth when applied to vaginal or oral mucosa. Such warming effect has been found to enhance intimacy and increase pleasure during intimate activities. Flavors and fragrances that enhance different senses and promote relaxation or intimacy may also be added to the compositions of this invention to enhance their effect, both in improving intimacy and in creating a feeling of relaxation.

The present compositions may be used to relieve vaginal dryness or dry mouth, to moisturize skin, to provide an ameliorating effect for frostbite or extremities overexposed to the cold and the like applications. The present compositions may be useful for treating conditions of infection on the skin or mucosa while soothing the area of infection.

The present compositions may also be used as vehicles to deliver medication or other treatment agents to biomembranes including, but not limited to, hormones, antimicrobials, antibacterials, antibiotics, non-steroidal anti-inflammatory agents, spermicides, immunodilators, anaesthetics, plant extracts, vitamins, corticosteroids or antifungal agents and the like and mixtures thereof.

Antifungal agents are preferably azoles or imidazoles, including by not limited to, miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubio, vorconazole, isoconazole, flutimazole, tioconazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

The present compositions, for example, for vulvovaginal or other mucosal use, may include one or more antibiotics including, but not limited to, metronidazole, clindamycin, tinidazole, ornidazole, secnidazole, refaximin, trospectomycin, purpuromycin and their pharmaceutically acceptable salts and the like and mixtures thereof.

The present compositions, for example, for vulvovaginal or other mucosal use, may include one or more antiviral agents including but are not limited to, immunomodulators, more preferably imiquimod, derivatives thereof, podofilox, podophyllin, interferon alpha, reticolos, cidofovir, nonoxynol-9, pharmaceutically acceptable salts thereof and the like and mixtures thereof.

The present compositions may include one or more spermicides including, but are not limited to, nonoxynol-9, octoxynol-9, dodecaethyleneglycol monolaurate, Laureth 10S, and Methoxypolyoxyethyleneglycol 550 Laurate and the like and mixtures thereof.

The present compositions may include antimicrobial agents, including but are not limited to, chlorohexidine gluconate, sodium polystyrene sulfonate, sodium cellulose sulfate, silver particles of micro- and sub-micrometer sizes, silver salts and other antibacterial agents known to the art and the like and mixtures thereof.

The present compositions may include local anesthetics, including but are not limited to, benzocaine, lidocaine, dibucaine, benzyl alcohol, camphor, resorcinol, menthol and diphenylhydramine hydrochloride and the like and mixtures thereof.

The present compositions may include plant extracts such as aloe, witch hazel, chamomile, hydrogentated soy oil and colloidal oatmeal, vitamins such as vitamin A, D or E and corticosteroids such as hydrocortisone acetate, and the like and mixtures thereof.

The present compositions, for example, for vulvovaginal or other mucosal use, may include one or more hormones for treating a decrease in estrogen secretion in the woman in need of estrogen replacement, such as women with vaginal atrophy. The hormones may include, but are not limited to, estrogen elected from the group consisting of estradiol, estradiol benzoate, estradiol cypionate, estradiol dipropinonate, estradiol enanthate, conjugated estrogen, estriol, estrone, estrone sulfate, ethinyl estradiol, estrofurate, quinestrol and mestranol and the like and mixtures thereof.

The present compositions may be useful for treating female sexual dysfunction by themselves as such compositions may serve to increase blood flow to areas on which such compositions are applied by increasing temperature thereon. Alternatively, the compositions may contain agents known to those of skill in the art to treat female sexual dysfunction (including different aspects of female sexual dysfunction such as female sexual arousal disorder, hypoactive sexual desire disorder, orgasmic disorder and the like) as well as those that treat dyspareunia and/or vaginismus or vulvodynia and to relieve pain upon intercourse. Such agents include hormones such as estrogen, prostaglandin, testosterone; calcium channel blockers, cholinergic modulators, alpha-adrenergic receptor antagonist, beta-adrenergic receptor agonists, camp-dependent protein kinase activators, superoxide scavengers, potassium channel activators, estrogen-like compounds, testosterone-like compounds, benzodiazepines, adrenergic nerve inhibitors, HMG-COA reductase inhibitors, smooth muscle relaxants, adrenosine receptor modulators and adenylyl cyclase activators. Such agents include phosphodiesterase-5 inhibitors and the like. The present compositions may also contain vasodilators such as methyl nicotinate, histamine hydrochloride and very small non-irritating amounts of methyl salicylate.

The present compositions, for example, for vulvovaginal use, may contain one or more analgesics and/or nonsteroidal anti-inflammatory agents for treating dysmenorrhea or menstrual cramping. The analgesics and nonsteroidal anti-inflammatory agents may include, but are not limited to, aspirin, ibuprofen, indomethacin, phenylbutazone, bromfenac, fenamate, sulidac, nabumetone, ketorolac, and naproxen and the like and mixtures thereof.

The present compositions, for example, for oral, vulvovaginal and/or other mucosal use, may enhance the absorption of active agents from the applied compositions into the mucosal membrane by increasing the composition and mucosal tissue temperature upon contact with the tissue.

The present compositions, for example, for vulvovaginal use, may prevent and/or treat dysmenorrhea by intravaginal warming or heating. Preferably, the composition heats the intravaginal area to a temperature preferably between about 37° C. and about 42° C., more preferably between about 38° C. and about 41° C. The compositions of the invention for use in such a method may optionally contain active agents such as analgesics and nonsteroidal anti-inflammatory agents for dysmenorrhea treatment. The composition of the invention may be administered directly into the vagina by an applicator, or be impregnated into vaginal devices such as tampon for intravaginal applications.

The present compositions may be manufactured as a coating of a tampon, or dispersing throughout the absorbent tampon material, or enclosed inside as a core of a tampon.

The present compositions may be applied to the oral or vaginal mucosal tissues manually or via a swab or vaginal applicator of in any way known to those of ordinary skill in the art.

In one particularly useful aspect of the present invention, the present lubricant compositions may be employed in the manufacture of a packaged condom product.

Such a method of manufacturing a condom product is included within the scope of the present invention and comprises providing a condom, for example a condom which comprises latex. The condom is contacted with a lubricant composition, for example in accordance with the present invention as described elsewhere herein, in an amount effective to lubricate the condom for use. Advantageously, both the inner wall of the condom and the outer wall of the condom are contacted and lubricated with the lubricant composition. The lubricated condom is placed in a package which is thereafter sealed to form a sealed package in which the condom and lubricant composition are substantially anhydrous.

The package is opened to remove the condom, which is then available for use, as desired.

A packaged condom product is also an aspect of the present invention and is included within the scope of the present invention. Such a packaged condom product is shown in FIG. 1.

Referring now to FIG. 1, the packaged condom product shown generally at 10 includes a sealed package 12, and a rolled condom 14. The package 12 is made of conventional polymeric packaging material and/or conventional metal foil packaging material.

The inner and outer walls of the condom 14, which is made of latex, are lubricated with a substantially clear lubricant composition in accordance with the present invention. Such lubricant, shown as 16 is advantageously substantially not stringy and has a control degree of tackiness, from the use of a PVP component or component portions, as described elsewhere herein in the lubricant composition.

The sealed package 12 includes front wall 15, back wall 17 and seals 18 and 20, which together form an outer perimeter region of the package. Either or both of the seals 18, 20 can be compromised to remove the condom from the package 12, for use, as desired.

The packaged condom product 10 is made using conventional condom manufacturing equipment in which the lubricant composition 16 is included with the condom during the normal course of manufacture, for example, in a manner substantially similar to that used to lubricate condoms with conventional condom lubricants.

One important advantage of the present invention is that the stringiness and/or tackiness of the lubricant compositions are controlled to facilitate the lubrication of and overall manufacturing efficiency of the final packaged condom product in a cost effective way, for example meeting satisfactory production rates while still providing the added advantage of providing a warming lubricant composition onto the condom. Thus, such warming is provided without substantial disruption to the condom manufacturing operation, for example, such an operation that is conventionally employed with conventional condom lubricants that are non-warming. This is an important advantage and provides substantial benefits, for example, increased user enjoyment, without substantially adding to the manufacturing cost of the packaged condom product.

The following non-limiting examples illustrate certain aspects of the present invention.

EXAMPLES 1 to 8

A series of eight (8) compositions were prepared for testing. These compositions were anhydrous and had chemical make-ups as shown in Table 1. The compositions were formed by combining or blending the ingredients together and stirring or mixing to obtain a uniform composition. The compositions of the present invention preferably are made from NF grade materials, which reduce the toxicity of the compositions.

Each of these compositions was tested in condom lubrication service. Briefly, commercial condom processing equipment was used during the testing. Each of the compositions was used during a trial run in which condoms were doubly lubricated, that is both the inner wall and the outer wall of the condom were lubricated, and the lubricated condoms were placed in individual packages which were then sealed.

TABLE 1

COMPOSITIONS

| INGREDIENT | 1 % by wt | 2 % by wt | 3 % by wt | 4 % by wt | 5 % by wt | 6 % by wt | 7 % by wt | 8 % by wt |
|---|---|---|---|---|---|---|---|---|
| PEG 400 (A) | 91.0 | 93.0 | 89.0 | 65.4 | 83.35 | 50.0 | 26.55 | 24.0 |
| PEG 200 (B) | — | — | — | 25.0 | 12.50 | 45.5 | 70.8 | 70.25 |
| BUTYLENE GLYCOL | — | — | — | — | — | — | — | — |
| LUVISKOL K90 (C) | 9.0 | 7.0 | 1.0 | 0.8 | — | — | — | — |
| LUVISKOL K30 (D) | — | — | 10.0 | 8.8 | — | — | — | — |
| KOLLIDON K17 (E) | — | — | — | — | — | — | 0.25 | 0.5 |
| KOLLIDON 30 (F) | — | — | — | — | 3.75 | 3.75 | 2.0 | 4.0 |
| KOLLIDON 90F (G) | — | — | — | — | 0.40 | 0.75 | 0.4 | 1.25 |
| VISCOSITY cps @25° C. | 10,800 | 5400 | 3250 | 1400 | 350 | 450 | 550-650 | 500-650 |

(A) Polyethylene glycol having a molecular weight of about 400 (Sold by BASF) (Equivalent products produced by Dow Chemical).
(B) Polyethlyene glycol having a molecular weight of about 200 (Sold by BASF) (Equivalent products produced by Dow Chemical).
(C) Polyvinylpyrrolidone having an average molecular weight of about 300,000-1,000,000 or about 360,000 (Sold by BASF) (Equivalent products produced by ISP).
(D) Polyvinylpyrrolidone having an average molecular weight of about 35,000-55,000 or about 40,000 (Sold by BASF) (Equivalent products produced by ISP).
(E) Polyvinylpyrrolidone having an average molecular weight of about 5,000-15,000 or about 10,000 (Sold by BASF) (Equivalent products produced by ISP).
(F) Polyvinylpyrrolidone having an average molecular weight of about 35,000-55,000 or about 40,000 (Sold by BASF) (Equivalent products produced by ISP).
(G) Polyvinylpyrrolidone having an average molecular weight of about 300,000-1,000,000 or about 360,000 (Sold by BASF) (Equivalent products produced by ISP).

A summary of the test results obtained with each of the compositions is as follows:

Composition 1: lubricant was completely clear and had a relatively dark yellow color; lubricant was too tacky and viscosity too high to maintain satisfactory condom production rate.

Composition 2: lubricant was completely clear and had a relatively dark yellow color; lubricant was too tacky and viscosity was still too high.

Composition 3: lubricant was completely clear and had a yellow color somewhat lighter than the color of Compositions 1 and 2; lubricant was still too viscous to maintain satisfactory condom production rate.

Composition 4: lubricant was completely clear and had a yellow color somewhat lighter than the color of Compositions 1 and 2; lubricant was still too viscous to maintain satisfactory condom production rate.

Composition 5: lubricant was completely clear and had a substantially water white color; lubricant had reduced viscosity, stringiness and tackiness relative to Composition 4; production equipment was marginally able to maintain satisfactory condom production rate using Composition 5.

Composition 6: lubricant was completely clear and had a substantially water white color; lubricant had reduced viscosity, stringiness and tackiness relative to Composition 4; production equipment was able to maintain satisfactory condom production rate using Composition 6.

Composition 7: lubricant was completely clear and had a substantially water white color; lubricant had reduced viscosity, stringiness and tackiness relative to Composition 4, and increased viscosity without increased stringiness relative to Composition 6; production equipment was able to maintain satisfactory condom production rate using Composition 7.

Composition 8: lubricant was completely clear and had a substantially water white color; lubricant had reduced viscosity, stringiness and tackiness relative to Composition 4, and increased viscosity without increased stringiness relative to Composition 6; production equipment was able to maintain satisfactory condom production rate using Composition 8.

These data indicate that the inclusion of relatively large amounts of polyvinylpyrrolidone component in the present lubricants results in the lubricants becoming yellow in color, with the higher molecular weight polyvinylpyrrolidone material providing a darker yellow color. The lubricants used on condoms and in condom manufacturing can have a degree of color and still be acceptable. Also, lubricants in accordance with the present inventions provided as separate or stand alone products may have a color other than water white and be acceptable. However, it is preferred, for example, in stand alone or separate lubricants, that such lubricants have a substantially water white color.

Composition 7 and 8 include a lower molecular weight polyvinylpyrrolidone. It has been found that such lower molecular weight polyvinylpyrrolidone, for example in combination with one or more, such as two, different higher molecular weight polyvinylpyrrolidones, as in Compositions 7 and 8, is useful to increase the viscosity of the lubricant without disadvantageously increasing the stringiness of the lubricant. Controlling or increasing the viscosity of the lubricant, for example, by including a lower molecular weight polyvinylpyrrolidone as shown in Composition 7 and 8, advantageously provides a lubricant which adheres better to the condom and/or provides a better feel or texture to the users of the condoms relative to a substantially identical lubricant having the same viscosity without the lower molecular weight polyvinylpyrrolidone.

EXAMPLES 9 TO 16

Each of the Compositions 1 to 8 is tested for heat generation efficacy relative to a commercially available product, in particular KY Warming Lubricant. Briefly, 50 grams of each of the Compositions 1 to 7 and KY Warming Lubricant is placed in a container holding 50 grams of water. Each mixture is stirred. The temperature of each mixture is monitored until the temperature reaches a steady value. That temperature is noted.

The temperature noted in this test with each of the Compositions 1 to 8 is higher than the temperature in the test with KY Warming Lubricant.

These results indicate that each of the Compositions 1 to 8 provide enhanced heat generation relative to KY Warming Lubricant.

It should be noted that the maximum temperature increase obtained by any warming lubricant varies depending on how much lubricant is used and the individual application in which the lubricant is used, among other factors. The tests and results presented here do, however, demonstrate that the Compositions 1 to 8 provide increased heat generation, on a per unit weight basis, relative to KY Warming Lubricant.

EXAMPLES 17 TO 20

Compositions 5, 6, 7 and 8 are each augmented with 2.0% by weight of miconazole nitrate. The resulting Compositions 9, 10, 11 and 12, respectively, are found in in vitro testing to be effective in killing anaenobes known to cause bacterial vaginal infections, and *Candida albicans*, known to cause vulvovaginal candidiasis. Thus, such augmented compositions can be used to treat or be a prophylactic against such infections by applying the composition to the affected area or area in question of the body.

While this invention has been described with respect to various specific examples and embodiments, it is to be understood that the invention is not limited thereto and that it can be variously practiced within the scope of the following claims.

What is claimed is:

1. A lubricant composition comprising:
a first polyethylene glycol component portion having a first molecular weight range; and
a second polyethylene glycol component portion having a second molecular weight range reduced relative to the first molecular weight range; and
an effective amount of a viscosity inducing component comprising a first polyvinylpyrrolidone component portion and a second polyvinylpyrrolidone component portion having a different average molecular weight than the first polyvinylpyrrolidone portion,
wherein the first and second polyvinylpyrrolidone component portions together are present in a combined concentration of from about 1% to about 15% by weight, the first and second polyethylene glycol component portions together comprise at least about 50% by weight of the composition and the second polyethylene glycol component portion is present in a greater amount by weight than the first polyethylene glycol component portion, the composition being substantially clear, uniform, smooth and substantially anhydrous, and being effective to generate heat when placed in contact with water,
wherein the weight ratio of the second polyethylene glycol component portion to the first polyethylene glycol component portion is from 1.1 to about 6.7,
and wherein said lubricant composition is substantially non-toxic and suitable for application as a personal lubricant to human skin or mucosal surfaces without causing undue irritation or harm, to increase pleasure during intimate activities.

2. The composition of claim 1 having a viscosity in a range of about 50 cps to less than 10,000 cps at 25° C.

3. The composition of claim 1 wherein the first polyethylene glycol component portion has a molecular weight range of about 350 to about 450 and the second polyethylene glycol component portion has a molecular weight range of about 150 to about 250.

4. The composition of claim 1 wherein the polyvinylpyrrolidone component includes a third polyvinylpyrrolidone component portion having a different average molecular weight than both the first and second portions.

5. The composition of claim 4 wherein the relative amounts of the first, second and third polyvinylpyrrolidone component portions are selected to be effective in controlling at least one of the tackiness of the composition and the stringiness of the composition, as desired.

6. A lubricant composition comprising:
  a first polyalkylene glycol component portion having a first molecular weight range; and a second polyalkylene glycol component portion having a second molecular weight range reduced relative to the first molecular weight range and the second polyalkylene glycol component portion is present in a greater amount by weight than the first polyalkylene glycol component portion, wherein the weight ratio of the second polyalkylene glycol component portion to the first polyalkylene glycol component portion is from about 1.1 to about 6.7; and
  an effective viscosity inducing amount of a polyvinylpyrrolidone component comprising a first polyvinylpyrrolidone component portion and a second polyvinylpyrrolidone component portion having a different average molecular weight than the first polyvinylpyrrolidone portion wherein, the first and second polyvinylpyrrolidone component portions together are present in a combined concentration of from about 1% to about 15% by weight, the first and second polyalkylene glycol components portions of different molecular weight ranges are comprised of the same polyalkylene glycol, the first and second polyalkylene component portions together comprising at least about 50% by weight of the composition, the composition being substantially clear, uniform, smooth and substantially anhydrous, and being effective to generate heat when placed in contact with water,
  and wherein said lubricant composition is substantially non-toxic and suitable for application as a personal lubricant to human skin or mucosal surfaces without causing undue irritation or harm, to increase pleasure during intimate activities.

7. The composition of claim 6 wherein the first and second polyalkylene glycol component portions are polyethylene glycol component portions.

8. The lubricant composition of claim 6 comprising a third polyvinylpyrrolidone component portion having a different and lower average molecular weight than both the first and second portions.

9. The composition of claim 8 wherein the polyalkylene glycol component comprises a polyethylene glycol component.

\* \* \* \* \*